Figure 4:
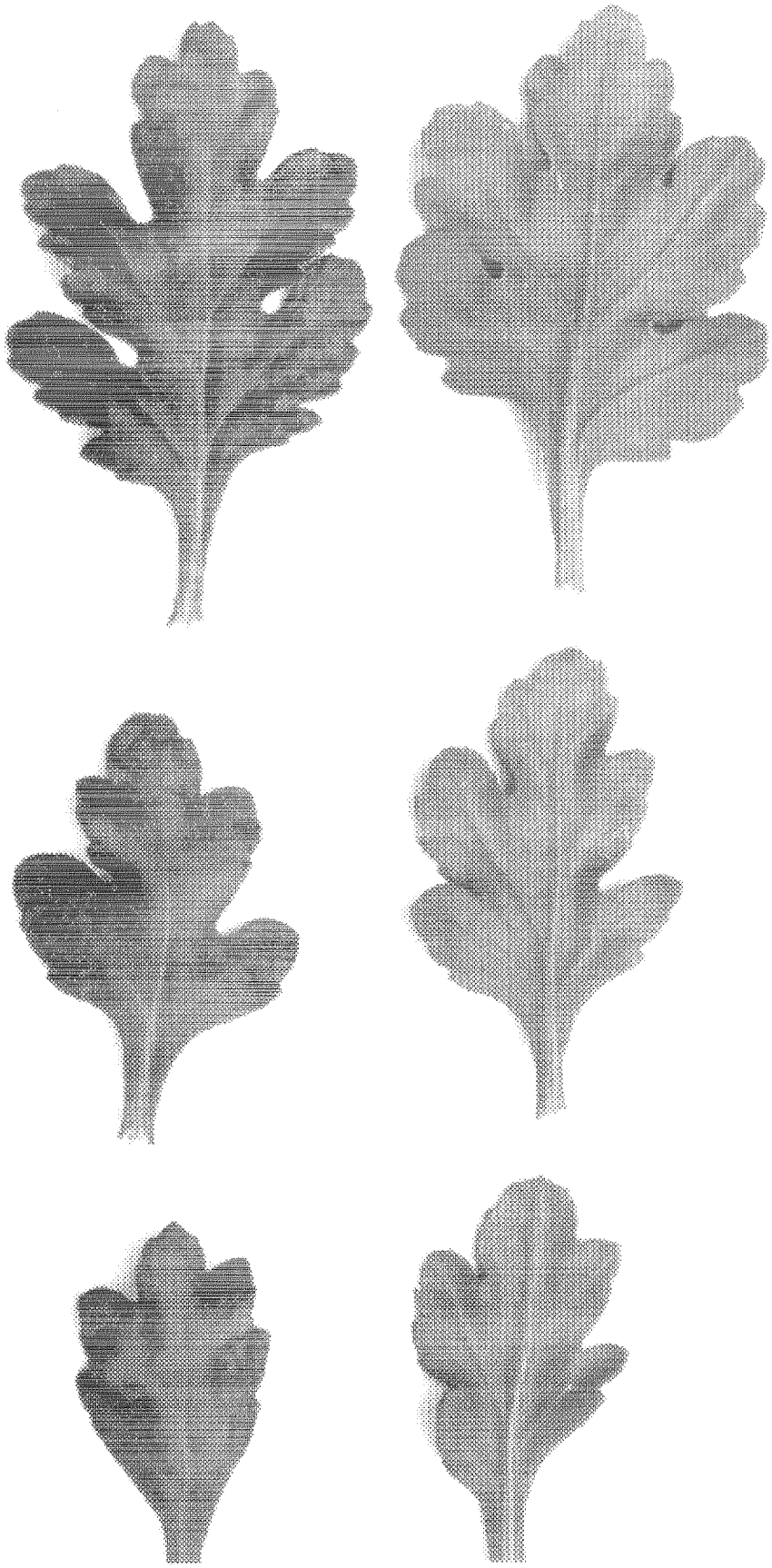

US00PP10223P

United States Patent [19]

VandenBerg

[11] Patent Number: Plant 10,223

[45] Date of Patent: Feb. 3, 1998

[54] CHRYSANTHEMUM PLANT NAMED 'FINESSE'

[75] Inventor: Cornelis P. VandenBerg, Salinas, Calif.

[73] Assignee: Yoder Brothers Inc., Barberton, Ohio

[21] Appl. No.: 772,491

[22] Filed: Dec. 23, 1996

[51] Int. Cl.[6] ..... A01H 5/00

[52] U.S. Cl. ..... Plt./74.1

[58] Field of Search ..... Plt./74.1, 82.3

[56] References Cited

U.S. PATENT DOCUMENTS

P.P. 9,702 11/1996 Polys ..... Plt./82.3

*Primary Examiner*—Howard J. Locker

*Attorney, Agent, or Firm*—C. A. Whealy

[57] ABSTRACT

A distinct cultivar of Chrysanthemum plant named 'Finesse', characterized by its rounded uniform plant habit; daisy spray-type inflorescences that are 3.2 to 3.8 cm in diameter; attractive red and yellow bi-colored ray florets and bright yellow disc florets; floriferousness with about 70 to 90 inflorescences per plant; and excellent postproduction longevity with inflorescences maintaining good substance and color for about four weeks in an interior environment.

3 Drawing Sheets

The present invention relates to a new and distinct cultivar of Chrysanthemum plant, botanically known as *Dendranthema grandiflora* and referred to by the cultivar name Finesse.

The new cultivar is a product of a planned breeding program conducted by the inventor in Salinas, Calif. The objective of the breeding program is to create new Chrysanthemum cultivars having inflorescences with desirable inflorescence forms and floret colors and good post-production longevity.

The new cultivar originated from a cross made by the inventor in February, 1993, of two unnamed proprietary seedling selections.

The cultivar 'Finesse' was discovered and selected by the inventor as a flowering plant within the progeny of the stated cross in a controlled environment in Salinas, Calif., in December, 1993. The selection of this plant was based on its desirable inflorescence form and floret colors and good post-production longevity.

Asexual reproduction of the new cultivar by terminal cuttings taken in a controlled environment in Salinas, Calif., has shown that the unique features of this new Chrysanthemum are stable and reproduced true to type in successive generations.

The cultivar 'Finesse' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Finesse'. These characteristics in combination distinguish 'Finesse' as a new and distinct cultivar:

1. Rounded uniform plant habit.
2. Daisy spray-type inflorescences that are 3.2 to 3.8 cm in diameter.
3. Attractive red and yellow bi-colored ray florets and bright yellow disc florets.
4. Very floriferous with about 70 to 90 inflorescences per plant.
5. Excellent postproduction longevity with inflorescences maintaining good substance and color for about four weeks in an interior environment.

The new Chrysanthemum is similar in ray floret color to the Chrysanthemum cultivar 'Bronze Cherie' (U.S. Plant Pat. No. 9,702). However in side-by-side comparisons in Salinas, Calif., under commercial practice, plants of the new Chrysanthemum differed from plants of the cultivar 'Bronze Cherie' in the following characteristics;

1. Plants of the new Chrysanthemum are not as freely branching as plants of the cultivar 'Bronze Cherie'.
2. Leaves of plants of the new Chrysanthemum have overlapping lateral lobes whereas leaves of plants of the cultivar 'Bronze Cherie' have divergent sinuses betwen lateral lobes.
3. Plants of the new Chrysanthemum flower slightly faster than plants of the cultivar 'Bronze Cherie'.
4. Plants of the new Chrysanthemum have slightly smaller inflorescences than plants of the cultivar 'Bronze'.
5. Ray florets of plants of the new Chrysanthemum are as distinct red and yellow bi-color whereas ray florets of plants of the cultivar 'Bronze Cherie' are a single bronze color.

The accompanying photographs illustrate the overall appearance of the new cultivar.

The first sheet is a colored photograph comprising a side perspective view of a typical flowering plant of 'Finesse'. This photograph shows the colors as true as it is reasonably possible to obtain in colored reproductions of this type. Floret and foliage colors in the photograph may differ from the actual colors due to light reflectance.

The second sheet is a black and white photograph comprising a top perspective view of inflorescences of the cultivar Finesse showing left to right: adaxial, abaxial and lateral surfaces.

The third sheet is a black and white photograph comprising a top perspective view of the abaxial (top of photo) and adaxial (bottom of photo) surfaces of leaves of the cultivar Finesse at three different stages of development, left to right: mature, intermediate and immature, showing the differences in size and lobation development.

In the following description, color references are made to The Royal Horticultural Society Colour Chart except where general terms of ordinary dictionary significance are used. The following observations and measurements describe plants grown in Leaminton, Ontario, Canada, under greenhouse conditions which approximate those generally used in commercial potted chrysanthemum production. Four unrooted cuttings were directly stuck in a 15-cm container. Measurements and numerical values represent averages for a minimum of four typical flowering containers.

Botanical classification: *Dendranthema grandiflora* cultivar Finesse.

Commercial classification: Daisy spray-type pot Chrysanthemum.

Parentage:

*Male or pollen parent.*—Unnamed proprietary seedlings selection.

*Female or seed parent.*—Unnamed proprietary seedling selection.

Propagation:

*Type.*—Terminal tip cuttings.

*Time to rooting.*—Seven to ten days with soil temperatures of 21C.

*Rooting habit.*—Fine, fibrous and well-branched.

Plant description:

*Appearance.*—Perennial herbaceous daisy spray-type pot Chrysanthemum. Upright, rounded habit and freely branching. Five to seven lateral branches develop after removal of terminal apex (pinching).

*Plant height.*—20 to 25 cm.

*Foliage description.*—Leaf arrangement: Alternate. Leaf size, fully expanded: Length: About 6.5 cm. Width: About 4.5 cm. Leaf apex: Obtuse. Leaf base: Attenuate. Leaf margin: Palmately lobed, lobes overlapping. Leaf texture: Abaxial and adaxial surfaces slightly pubescent. Veins prominent on abaxial surface. Color: Young foliage adaxial surface: 147A. Young foliage abaxial surface: 147B. Mature foliage adaxial surface: 147A. Mature foliage abaxial surface: 147B. Venation adaxial surface: 147B. Venation abaxial surface: 147B.

Inflorescence description:

*Appearance.*—Single daisy-type inflorescence form with oblong red and yellow bi-colored ray florets. Inflorescences borne on terminals above foliage, arising from leaf axils. Disk and ray florets arranged acropetally on a capitulum.

*Flowering response.*—Under natural conditions, plants flower in the autumn/winter in the Northern Hemisphere. At other times of the year, inflorescence initiation and development can be induced under short day/long night conditions (at least 13.5 hours of darkness). Plants exposed to 1.5 to 2 weeks of long day/short night conditions after planting followed by photoinductive short day/long night conditions flower about 46 to 52 days later.

*Postproduction longevity.*—In an interior environment, inflorescences will maintain good color and substance for about four weeks.

*Quantity of inflorescences.*—Very floriferous with about 14 inflorescences per flowering lateral stem, or about 70 to 90 inflorescences per plant.

*Inflorescence size.*—Diameter: 3.2 to 3.8 cm. Depth (height): About 1 cm. Diameter of disc: About 1.5 cm.

*Ray florets.*—Shape: Oblong, straight, very short corolla tube. Size: Length: About 2 cm. Width: About 7 mm. Apex: Obtuse. Margin: Entire. Texture: Ribbed, smooth, glabrous. Aspect: Flat. Orientation: Positioned perpendicular to the penduncle. Number of ray florets per inflorescence: About 22. Color: Adaxial surface: 34A/34B, base 15C. Abaxial surface: 15D streaked with 34A.

*Disc florets.*—Shape: Tubular, apex fringed. Size: Length: About 5 mm. Width: Apex: About 2 mm. Base: About 1 mm. Number of disc florets per inflorescence: About 115. Color: Immature: 154A. Mature: Apex: 9A. Base: 154A.

*Peduncle.*—Aspect: Flexible, angled about 45° to the stem. Length: First peduncle: About 2 cm. Fourth peduncle: About 2.5 cm. Texture: Pubescent. Color: 143A.

*Reproductive organs.*—Androecium: Present on disc florets only. Anther color: 9A. Pollen: Moderate to abundant, 9A in color. Gynoecium: Present on both ray and disc florets.

Disease resistance: No known Chrysanthemum diseases observed to date on plants grown under commercial greenhouse conditions.

Seed production: Seed production has not been observed.

It is claimed:

1. A new and distinct cultivar of Chrysanthemum plant named 'Finesse', as illustrated and described.

* * * * *

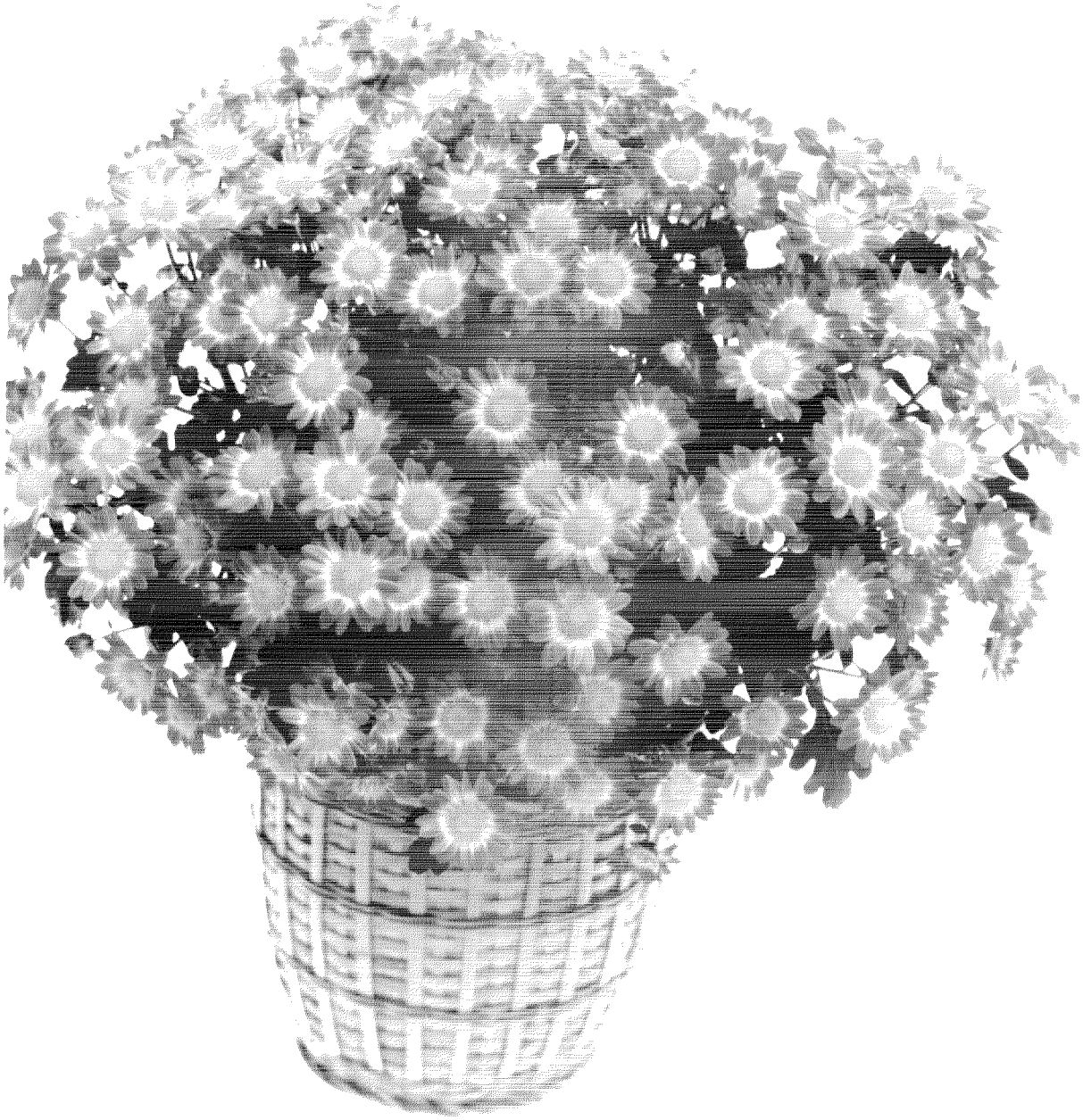

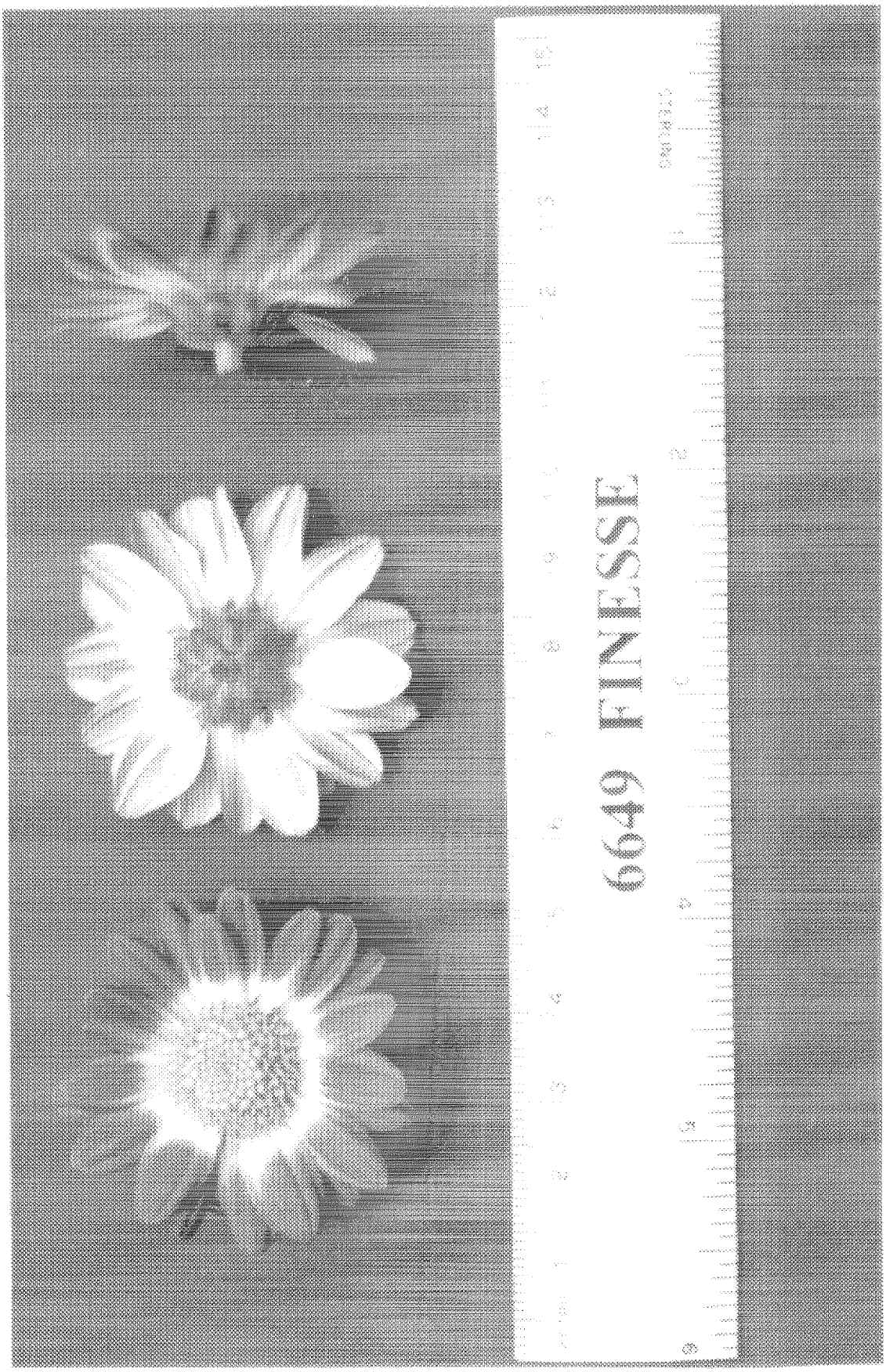
6649 FINESSE